United States Patent [19]

Garwin

[11] Patent Number: 5,248,505
[45] Date of Patent: Sep. 28, 1993

[54] METHOD FOR TREATING GASTROINTESTINAL DISTRESS

[75] Inventor: Jeffrey L. Garwin, Paoli, Pa.

[73] Assignee: McNeil-PPC, Inc., Milltown, N.J.

[21] Appl. No.: 852,355

[22] Filed: Mar. 17, 1992

Related U.S. Application Data

[63] Continuation of Ser. No. 430,707, Nov. 1, 1989, abandoned.

[51] Int. Cl.⁵ .................. A61K 9/24; A61K 31/74; A61K 31/695; A61K 31/54
[52] U.S. Cl. .................. 424/472; 424/78.01; 424/475; 514/63; 514/161; 514/188; 514/327; 514/278; 514/456; 514/819; 514/820; 514/867; 514/330
[58] Field of Search ............ 514/63, 188, 161, 278, 514/228, 441, 456, 819, 820, 867; 424/78.01, 472, 475

[56] References Cited

U.S. PATENT DOCUMENTS

| | | | |
|---|---|---|---|
| 2,441,098 | 5/1948 | Hyde | 556/456 |
| 2,898,340 | 8/1959 | Janssen | 546/228 |
| 2,951,011 | 12/1956 | Feinstone | 424/474 |
| 4,676,984 | 6/1987 | Wu et al. | 424/689 |
| 4,786,502 | 11/1988 | Chapura | 424/441 |

FOREIGN PATENT DOCUMENTS

| | | |
|---|---|---|
| 2611979 | 3/1976 | Fed. Rep. of Germany . |
| 2565107 | 5/1984 | France . |
| 209713 | 9/1984 | New Zealand . |
| 1097955 | 9/1965 | United Kingdom . |

OTHER PUBLICATIONS

Mims Annual, 1989, Section 1e Antidiarrhoels, pp. 1-19.
Naresh K. Jain et al. "Activated Charcoal, Simethicone & Intestinal Gas: A Double-Blind Study", Annals of Internal Machine, vol. 105, No. 1 (Jul. 1986) pp. 61-62.
Carlos H. Lifschitz et al. "Effect of a Simethicone-Containing Tablet on Colonic Gas Elimination in Breath" Digestive Diseases & Science, vol. 30, No. 5 (May 1985) pp. 426-430.
Michael M. Van Ness et al, Flatulence: Pathophysiology & Treatment, AFP Practical Therapeutics, vol. 31, No. 4 (Apr. 1985) pp. 198-207.
J. A. Rider & H. C. Moeller, Use of Silicone in the Treatment of Intestinal Gas & Bloating, J.A.M.A., Dec. 17, 1960, pp. 106-108.
J. A. Rider, Intestinal Gas & Bloating: Treatment with Methyl Polysiloxane, Amer. Practit 11:52-57 (Jan. 1960).
Longe, R. L.: Antidiarrheal and Other Gastrointestinal Products, in Chapter 5 of the Handbook of Nonprescription Drugs, 8th Ed.
Hillebrand, I., Boehme, K., and Berchtold, P.: The Influence of Dimeticone and Guar on Intestinal Symptoms Induced by Acarbose.

Primary Examiner—Frederick E. Waddell
Assistant Examiner—K. Weddington

[57] ABSTRACT

This invention relates to a pharmaceutical composition for treating gastrointestinal distress comprising an effective amount of an antidiarrheal composition, e.g. loperamide, and an antiflatulent effective amount of simethicone and methods of treating gastrointestinal distress comprising administering such pharmaceutical compositions.

16 Claims, No Drawings

METHOD FOR TREATING GASTROINTESTINAL DISTRESS

This is a continuation of application Ser. No. 07/430,707, filed Nov. 1, 1989, now abandoned, the text of which is hereby incorporated by reference.

FIELD OF THE INVENTION

This invention relates to a pharmaceutical composition for treating gastrointestinal distress comprising an effective amount of an antidiarrheal composition and an antiflatulent effective amount of simethicone and methods of its use.

BACKGROUND OF THE INVENTION

Gastrointestinal distress for the purposes of the present invention is defined as discomfort associated with an intestinal disorder characterized by symptoms of diarrhea and flatulence or gas. Diarrhea is the abnormally frequent passage of watery stool.

Diarrhea may have a variety of causes including bacteria or viral induced diarrhea. Travelers diarrhea, for example, is also believed to be of microbial origin. Diarrhea may also be a side effect of drug administration, particularly antibiotics. Diarrhea may be induced by food intolerance which is caused by allergy or the ingestion of foods that are excessively fatty, spicy, or contain a high degree of fermentable carbohydrate, roughage or a large number of seeds. Food intolerance may also be brought on by a preformed toxin in the food thus causing food poisoning. Other conditions and diseases can also cause diarrhea, and diarrhea may only be one of many symptoms associated with a major illness.

Diarrhea is thus a symptom of an intestinal disorder or other bodily function and symptomatic relief can be accomplished by the use of various prescription and nonprescription products. The active ingredients in these products include loperamide, attapulgite, bismuth subsalicylate, diphenoxylate HCl, polycarbophil, calcium polycarbophil and mixtures thereof.

Flatulence or intestinal gas is another intestinal disorder which contributes to gastrointestinal distress. Such gas exists as trapped gas bubbles which manifest feelings of pain, bloating and cramping in the abdominal area. It has been surprisingly found in a study of people complaining of diarrhea that about 67% of the population study also complained of accompanying gas.

While various products exist for separately treating diarrhea and gas, no product has heretofore been proposed for treating the combination of the symptoms of both diarrhea and gas which has been defined herein as gastrointestinal distress. It is therefore an object of the present invention to provide a composition for the treatment of gastrointestinal distress in response to a long felt need which has now been recognized by the above-mentioned study.

SUMMARY OF THE INVENTION

The foregoing object of fulfilling a long felt need for a Pharmaceutical composition which can relieve the symptoms of gastrointestinal distress, i.e. diarrhea and flatulence has now been accomplished in accordance with the compositions and methods of the present invention.

In accordance with the purposes of the invention as embodied and fully described herein, the invention comprises a pharmaceutical composition for treating gastrointestinal distress comprising an effective amount of an antidiarrheal compound and an antiflatulent effective amount of simethicone. In preferred embodiments the antidiarrheal compound is selected from the group consisting of loperamide, attapulgite, bismuth subsalicylate, diphenoxylate HCl, polycarbophil, calcium polycarbophil and mixtures thereof. In more preferred embodiments the antidiarrheal compound is loperamide.

As embodied and broadly described herein, the invention further comprises a method for treating gastrointestinal distress comprising administering a combination pharmaceutical composition to a patient comprising an effective amount of an antidiarrheal and an antiflatulent effective amount of simethicone. In preferred embodiments of the method of the invention, the antidiarrheal composition is selected from those described above with loperamide being particularly preferred.

DETAILED DESCRIPTION OF PREFERRED EMBODIMENTS OF THE INVENTION

Reference will now be made in detail to preferred embodiments of the invention, examples of which are illustrated in the following examples section.

To achieve the object of the invention of providing a pharmaceutical composition for treating gastrointestinal distress, an effective amount of an antidiarrheal compound is combined with an antiflatulent effective amount of simethicone.

The preferred antiflatulent composition combined with effective amounts of an antidiarrheal compound in accordance with the invention is simethicone, also known as polydimethylsiloxane. Simethicone is a surface active agent which acts as a defoamer or dispersent of gas bubbles by changing the surface tension of the bubbles to enable them to coalesce. The defoaming action of simethicone relieves flatulence by dispersing and preventing the formation of mucous surrounded gas pockets in the gastrointestinal tract. By reducing the size of the gas bubbles, the gas is free to travel through the gastrointestinal tract for release by belching or passing flatus. This release thus relieves the pain and pressure commonly associated with the presence of gas in the gastrointestinal tract.

Simethicone acts largely in the stomach but is also believed to have gas relieving effect in the intestines. Since simethicone is not absorbed or metabolized by the body, if released in the stomach area, it will proceed through the gastrointestinal tract into the intestines. In preferred embodiments of the composition of the invention, simethicone is presented in an immediate release form that is released in the stomach area. Enteric coated simethicones or a combination of immediate release and enteric coated simethicones may be included in accordance with the present invention to release the simethicone in the intestines.

The preferred dosage ranges for simethicone is in the range of about 20 to 125 mg. per dosage unit, generally not to exceed 500 mg/day. The dosage ranges may vary for age and weight of a patient as well as the severity of symptoms.

Effective amount of antidiarrheal compositions combined with effective amounts of simethicone vary with the particular antidiarrheal composition selected. The preferred antidiarrheal compositions and their preferred dosage ranges as a component of the composition in accordance with the invention are as follows: loperamide with a dosage range from about 0.5 mg. to 8.0 mg.; attapulgite with a dosage range from about 300 mg. to 1600 mg.; bismuth subsalicylate with a dosage range from about 120 mg. to 1200 mg; diphenoxylate HCl with a preferred dosage range from about 0.7 mg. to 10 mg.; polycarbophil with a preferred dosage range of about 150 to 2000 mg.; and calcium polycarbophil with a preferred dosage range of about 150 to 2000 mg. Compatible mixtures of these antidiarrheal compositions and their pharmaceutically acceptable salts can also be included in a pharmaceutical composition of the invention.

Loperamide is the most preferred antidiarrheal active for use in the pharmaceutical composition of the invention. Loperamide as a component of the present invention includes pharmaceutically acceptable salts of loperamide such as loperamide HCl. Loperamide acts by slowing intestinal motility and by normalizing water and electrolyte movement through the bowel. Further, loperamide inhibits peristaltic activity by a direct effect on circular and longitudinal muscles of the intestinal walls. Loperamide in man thus prolongs the transit time of the intestinal contents and reduces the daily fecal volume and increases the viscosity and bulk density and thus diminishes loss of foods and electrolytes.

Dosage ranges chosen for the loperamide component of the composition of the present invention depend upon the age and weight of the Patient. A preferred adult dose given initially for the treatment of gastrointestinal distress is 4 mg. followed by 2 mg. after each unformed stool until diarrhea is controlled. A preferred ratio of simethicone to loperamide is in the range of from about 100 to 1 to about 10 to 1. Loperamide acts in the intestines and is therefore preferably enteric coated so that it will pass through the stomach and be released in the small intestines. While enteric coating is preferred, it is not essential since loperamide will not be absorbed or metabolized in the stomach but will eventually pass through into the small intestines in any event.

Other ingredients both active and inactive can be added to the combination antidiarrheal/antiflatulence compositions of the invention. For example, flavoring compositions are desirably added to chewable and liquid dosage forms. The composition of the invention can also be provided in an oral solid dosage form.

Antispasmodic and anticholinergic compositions and their pharmaceutically acceptable salts may, for example, be added to the compositions of the invention. Examples of antispasmodics include phenobarbital, dicyclomine HCl, belladonna alkaloids, and atropine. Further, various digestive enzymes such as lipase, amylase and protease may also be provided as additional components in combination with the compositions of the invention to reduce and relieve gastrointestinal distress.

A method of treating gastrointestinal distress is also provided in accordance with the present invention. The method comprises administering a combination pharmaceutical composition in accordance with the invention to a patient having the symptoms of gastrointestinal distress which is a combination of diarrhea and flatulence, including discomforts associated with flatulence which may include bloating, pain, and uncomfortable fullness. The method comprises treating the patient with an effective amount of an antidiarrheal composition and an antiflatulent effective amount of simethicone. The antidiarrheal is preferably selected from the group consisting of loperamide, attapulgite, bismuth subsalicylate, polycarbophil, calcium polycarbophil and mixtures thereof. More preferably, the antidiarrheal composition is loperamide in a dosage range of about 0.5 to 8.0 mg. combined with from about 20 to 125 mg. of simethicone.

EXAMPLES

The invention will now be illustrated by examples. The examples are not intended to be limiting of the scope of the present invention but read in conjunction with the detailed and general description above, provide futher understanding of the present invention and an outline of a process for preparing the compositions of the invention.

EXAMPLE I

Bi-layer Loperamide HCl 2 mg./Simethicone 80 mg., Chewable Tablet

| Ingredients | mg/tablet |
|---|---|
| SIMETHICONE LAYER | |
| dicalcium phosphate. NF | 784.000 |
| collodial silicon dioxide. NF | 40.000 |
| simethicone. USP | 80.000 |
| aspartame. NF | 5.000 |
| flavors | 16.056 |
| stearic acid. NF | 18.879 |
| Layer Total | 943.935 |
| LOPERAMIDE LAYER | |
| loperamide HCl, USP | 2.000 |
| sucrose. NF | 12.000 |
| mannitol, USP | 565.120 |
| aspartame, NF | 2.820 |
| flavors | 9.060 |
| stearic acid. NF | 6.000 |
| colloidal silicon dioxide, NF | 3.000 |
| Layer Total | 600.000 |
| Bi-layer Tablet Total | 1541.935 |

Manufacturing Instructions

A. Simethicone Granulation

Combine dicalcium phosphate, colloidal silicon dioxide, simethicone, aspartame, flavors and stearic acid. Mix using an appropriate mixer (e.g., PK Blender) for 10 minutes.

B. Loperamide Granulation

Granulate loperamide HCl with sucrose and a portion of the mannitol using an appropriate fluid bed granulator (i.e., Glatt GPCG-3).

Dry blend stearic acid, colloidal silicon dioxide, aspartame, flavors and the remaining mannitol with the above granulation. Mix for 10 minutes in an appropriate mixer (e.g., PK Blender).

C. Compression

Compress the loperamide and simethicone granulations as separate layers using a bi-layer tablet press (e.g., Stokes Versa Press).

EXAMPLE II

Bi-layer Loperamide HCl 2 mg./Simethicone 80 mg. Swallowable Caplet

| Ingredients | mg/tab |
|---|---|
| SIMETHICONE LAYER | |
| dicalcium phosphate, NF | 784.000 |
| collodial silicon dioxide, NF | 40.000 |
| simethicone. USP | 80.000 |
| sodium starch glycolate, NF | 80.360 |
| stearic acid, NF | 20.090 |
| Layer Total | 1004.450 |

-continued

| Ingredients | mg/tab |
| --- | --- |
| LOPERAMIDE LAYER | |
| loperamide HCl, USP | 2.000 |
| mannitol, USP | 101.000 |
| sucrose, NF | 12.000 |
| microcrystalline cellulose, NF | 6.460 |
| sodium starch glycolate, NF | 3.880 |
| stearic acid, NF | 1.290 |
| colloidal silicon dioxide, NF | 0.646 |
| Layer Total | 129.276 |
| Bi-layer Caplet Total | 1133.7260 |

Manufacturing Instructions

A. Simethicone Granulation

Combine dicalcium phosphate, colloidal silicon dioxide, simethicone, sodium starch glycolate and stearic acid. Mix using an appropriate mixer (e.g., PK Blender) for 10 minutes.

B. Loperamide Granulation

Granulate loperamide HCl with sucrose and a portion of the mannitol using an appropriate fluid bed granulator (e.g., Glatt GPCG-3).

Dry blend stearic acid, colloidal silicon dioxide, microcrystalline cellulose and sodium starch glycolate with the above granulation and mix for 10 minutes using an appropriate mixer (e.g., PK Blender).

C. Compression

Compress the loperamide and simethicone granulations as separate layers using an appropriate bi-layer tablet press (e.g., Stokes Versa Press).

EXAMPLE III

Loperamide 2 mg./Simethicone 80 mg. Emulsion

| Ingredients | mg/tab |
| --- | --- |
| sucrose, NF | 35.00 |
| sorbitol, USP (70%) | 20.00 |
| sodium benzoate, NF | 0.10 |
| benzoic acid, USP | 0.10 |
| citric acid, USP (Anydrous) | 0.032 |
| propylene glycol, USP | 15.00 |
| glycerin, USP | 15.00 |
| carboxy polymethylene, NF | 0.20 |
| loperamide HCl, USP | 0.02 |
| 30% simethicone emulsion | 0.80 |
| 10% sodium hydroxide solution | 0.80 |
| purified water, USP, qs to: | 100.00 ml |

Manufacturing Instructions

Combine the above ingredients (except 10% sodium hydroxide solution) with mixing. Add with gentle mixing, 10% sodium hydroxide solution.

QS to final volume with purified water and mix (e.g. IKA-Werk mixer at low speed).

EXAMPLE IV

Bismuth Subsalicylate 300 mg/Simethicone 80 mg Emulsion/Suspension

Example IV is carried out using the same ingredients and procedure as used for the emulsion of Example III except that 3.00 gm % bismuth subsalicylate is substituted for 0.02 gm % loperamide.

EXAMPLE V

Loperamide 2 mg/Bismuth Subsalicylate 300 mg./Simethicone 80 mg. Emulsion/Suspension Example V is carried out using the same ingredients and procedure as used for the emulsion of Example III except that 3.00 gm % bismuth subsalicylate is added to the emulsion.

Method of Treating Patients with Gastrointestinal Distress

A patient exhibiting the symptoms of gastrointestinal distress, i.e. diarrhea and excess gas or flatulence, is treated by the administration of two caplets of the loperamide/simethicone composition in accordance with Example II whereby each caplet contains 2 mg. of loperamide and 80 mg. of simethicone as an initial dose followed by administering an additional caplet after each unformed stool not to exceed 8 mg loperamide per day (4 caplets), one caplet being a dosage of 2 mg. of loperamide and 80 mg. of simethicone.

The scope of the present invention is not limited by the description, examples, and suggested uses herein, and modifications can be made without departing from the spirit of the invention. For example, the combined antidiarrheal and antiflatulent compositions of the invention may be provided in a sustained release formulation for treatment of chronic gastrointestinal distress.

Application of the compositions and methods of the present invention for medical and pharmaceutical uses can be accomplished by any clinical, medical and pharmaceutical method and technique as are presently or prospectively known to those skilled in the art. Thus it is intended that the present invention cover the modifications and variations of this invention provided that they come within the scope of the appended claims and their equivalents.

What is claimed is:

1. A method for treating a human suffering from an intestinal disorder characterized by the symptoms of diarrhea and flatulence or gas comprising administering to said human in a combined pharmaceutical composition, an effective amount of an antidiarrheal compound selected from the group consisting of loperamide, bismuth subsalicyclate, diphenoxylate, polycarbophil, their pharmaceutically acceptable salts and mixtures thereof; and an antiflatulent effective amount of simethicone.

2. The method of claim 1 wherein the amount of simethicone administered is in the range of from about 20 mg to about 125 mg per dosage unit.

3. The method of claim 2 wherein the amount of loperamide administered is in a dosage range of from about 0.5 mg to about 8.0 mg.

4. The method of claim 3 wherein the loperamide is administered in the form of a hydrochloride salt.

5. The method of claim 2 wherein the amount of bismuth subsalicylate administered is in a dosage range of from about 120 mg to about 1200 mg.

6. The method of claim 2 wherein the amount of diphenoxylate administered is in a dosage range of from about 0.7 mg to about 10 mg.

7. The method of claim 6 wherein the diphenoxylate is administered in the form of a hydrochloride salt.

8. The method of claim 2 wherein the amount of polycarbophil is in a dosage range of from about 150 mg to about 2000 mg.

9. The method of claim 8 wherein the polycarbophil is provided as calcium polycarbophil.

10. The method of claim 3 wherein the loperamide administered is provided in an enterically coated form.

11. The method of claim 10 wherein the loperamide and simethicone are provided in a solid dosage form.

12. The method of claim 11 wherein the solid dosage form consisting of at least a first layer and a second layer and the enterically coated loperamide is present in the first layer and the simethicone is present in the second layer.

13. The method of claim 2 wherein the amount of simethicone administered is 80 mg per dosage unit and the amount of loperamide administered is 2 mg per dosage unit.

14. The method of claim 2 wherein the amount of simethicone administered is 125 mg per dosage unit and the amount of loperamide administered is 2 mg per dosage unit.

15. The method of claim 2 wherein the amount of bismuth subsalicyclate administered is 300 mg per dosage unit and the amount of simethicone administered is 80 mg per dosage unit.

16. A method for treating a human suffering from an intestinal disorder characterized by diarrhea and flatulence and or gas comprising administering to said human in a combined pharmaceutical composition, 4 mg of loperamide and an antiflatulent effective amount of simethicone; thereafter administering to said human in a combined pharmaceutical composition, 2 mg of loperamide and an antiflatulent effective amount of simethicone until the diarrhea is controlled.

* * * * *